(12) United States Patent
Kiani et al.

(10) Patent No.: US 7,962,188 B2
(45) Date of Patent: Jun. 14, 2011

(54) ROBUST ALARM SYSTEM

(75) Inventors: Massi Joseph E. Kiani, Laguna Niguel, CA (US); Mohamed Kheir Diab, Mission Viejo, CA (US); Marcelo M. Lamego, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 446 days.

(21) Appl. No.: 11/546,927

(22) Filed: Oct. 12, 2006

(65) Prior Publication Data

US 2007/0109115 A1      May 17, 2007

Related U.S. Application Data

(60) Provisional application No. 60/726,638, filed on Oct. 14, 2005.

(51) Int. Cl.
    *A61B 5/1455*      (2006.01)
(52) U.S. Cl. .......................................... 600/310; 600/300
(58) Field of Classification Search ................. 600/310, 600/322, 323, 300
See application file for complete search history.

(56) References Cited

U.S. PATENT DOCUMENTS

| | | | |
|---|---|---|---|
| 4,037,222 A | 7/1977 | Solomon | |
| 4,745,398 A * | 5/1988 | Abel et al. | 340/500 |
| 4,785,285 A * | 11/1988 | Teich et al. | 340/518 |
| 4,843,378 A | 6/1989 | Kimura | |
| 4,960,128 A | 10/1990 | Gordon et al. | |
| 4,964,408 A | 10/1990 | Hink et al. | |
| 5,029,290 A * | 7/1991 | Parsons et al. | 340/533 |
| 5,041,187 A | 8/1991 | Hink et al. | |
| 5,069,213 A | 12/1991 | Polczynski | |
| 5,103,214 A | 4/1992 | Curran | |
| 5,163,438 A | 11/1992 | Gordon et al. | |
| 5,337,744 A | 8/1994 | Branigan | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,652,566 A * | 7/1997 | Lambert | 340/507 |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |

(Continued)

*Primary Examiner* — Eric F Winakur

(74) *Attorney, Agent, or Firm* — Knobbe, Martens, Olson & Bear LLP

(57) ABSTRACT

A robust alarm system has an alarm controller adapted to input an alarm trigger and to generate at least one alarm drive signal in response. Alarm subsystems input the alarm drive signal and activate one or more of multiple alarms accordingly. A subsystem function signal provides feedback to the alarm controller as to alarm subsystem integrity. A malfunction indicator is output from the alarm controller in response to a failure within the alarm subsystems.

11 Claims, 10 Drawing Sheets

U.S. PATENT DOCUMENTS

| | | | |
|---|---|---|---|
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,865,736 A * | 2/1999 | Baker et al. | 600/323 |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,279,377 B1 * | 8/2001 | Cao | 73/23.31 |
| 6,280,213 B1 | 8/2001 | Tobler et al. | |
| 6,285,896 B1 | 9/2001 | Tobler et al. | |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,585 B1 | 4/2004 | Parker | |
| 6,725,075 B2 | 4/2004 | Al-Ali | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Al et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,292,141 B2 * | 11/2007 | Staats et al. | 600/300 |
| 2002/0161291 A1 * | 10/2002 | Kianl et al. | 600/324 |
| 2003/0034885 A1 * | 2/2003 | Catton et al. | 340/506 |
| 2003/0125612 A1 * | 7/2003 | Fox et al. | 600/347 |
| 2003/0137423 A1 * | 7/2003 | Al-Ali | 340/573.1 |

\* cited by examiner

US 7,962,188 B2

ROBUST ALARM SYSTEM

REFERENCE TO RELATED APPLICATION

The present application claims priority benefit under 35 U.S.C. §119(e) from U.S. Provisional Application No. 60/726,638, filed Oct. 14, 2005, entitled "Robust Alarm System," which is incorporated herein by reference.

BACKGROUND OF THE INVENTION

Physiological measurement systems employed in healthcare often feature visual and audible alarm mechanisms that alert a caregiver when a patient's vital signs are outside of predetermined limits. For example, FIG. 1 illustrates a pulse oximeter, which measures the oxygen saturation level of arterial blood, an indicator of oxygen supply. A typical pulse oximetry system 100 has a sensor 101 that provides a sensor signal 162 to a pulse oximeter (monitor) 102. The sensor 101 has emitters 110 and a detector 120 and is attached to a patient at a selected fleshy tissue site, such as a fingertip. The emitters 110 transmit light having red and IR wavelengths into the tissue site. The detector 120 generates the sensor signal 162 in response to the intensity of the emitter transmitted light after attenuation by pulsatile blood flow within the tissue site A pulse oximetry sensor is described in U.S. Pat. No. 6,088,607 entitled Low Noise Optical Probe, which is assigned to Masimo Corporation, Irvine, Calif. and incorporated by reference herein.

The monitor 102 has drivers 140, a controller 150 and a front-end 160. The drivers 140 activate the emitters 110 according to the controller 150, and the front-end 160 conditions and digitizes the resulting sensor signal 162. The monitor 102 also has a signal processor 170, a display 180 and an alarm 190. The signal processor 170 inputs the conditioned and digitized sensor signal 164 and calculates oxygen saturation along with pulse rate, as is well-known in the art. The display 180 provides a numerical readout of a patient's oxygen saturation and pulse rate. The alarm 190 provides an audible indication when oxygen saturation or pulse rate are outside of preset limits. A pulse oximetry monitor is described in U.S. Pat. No. 5,482,036 entitled Signal Processing Apparatus and Method, which is assigned to Masimo Corporation, Irvine, Calif. and incorporated by reference herein.

SUMMARY OF THE INVENTION

Alarm reliability is a critical requirement for physiological measurement systems employed in healthcare. An alarm failure may result in patient injury or death. A robust alarm system provides at least one of redundant alarms, drive circuit integrity checks and alarm integrity checks so as to increase alarm reliability.

One aspect of a robust alarm system comprises an alarm controller adapted to input an alarm trigger and generate at least one alarm drive signal in response. Alarm subsystems are adapted to input the alarm drive signal and activate alarms in response. A subsystem function signal is output from the alarm subsystems to the alarm controller so as to indicate the integrity of the alarm subsystems. A malfunction indicator is output from the alarm controller in response to a failure within the alarm subsystems.

In one embodiment, the alarm subsystems have one or more of a driver, a circuit tester and an alarm detector. The driver and a corresponding drive circuit actuates one or more alarms in response to the alarm drive signal. A circuit tester verifies the integrity of the driver and drive circuit. An alarm detector verifies the integrity of at least one of the alarms. Alarm detection may be based upon detecting emitted sound waves or by detecting alarm transducer movement or vibration utilizing ultrasound, optical or piezoelectric sensors to name a few.

Another aspect of a robust alarm system comprises a processor responsive to a sensor so as to initiate an alarm trigger based upon a physiological event. A controller is responsive to the alarm trigger so as to generate at least one alarm drive signal. Multiple alarms are in communication with the alarm drive signal so as to concurrently indicate the physiological event.

A further aspect of a robust alarm system is a method where optical radiation having at least two wavelengths is transmitted into a tissue site. A sensor signal is provided in responsive to attenuation of the optical radiation by pulsatile blood flowing within the tissue site. A physiological parameter measurement is derived from the sensor signal, and an alarm trigger is generated in response to the measurement being outside of predetermined limits for the parameter. Multiple alarms are concurrently activated in response to the alarm trigger.

DETAILED DESCRIPTION OF THE PREFERRED EMBODIMENTS

Figure 1:
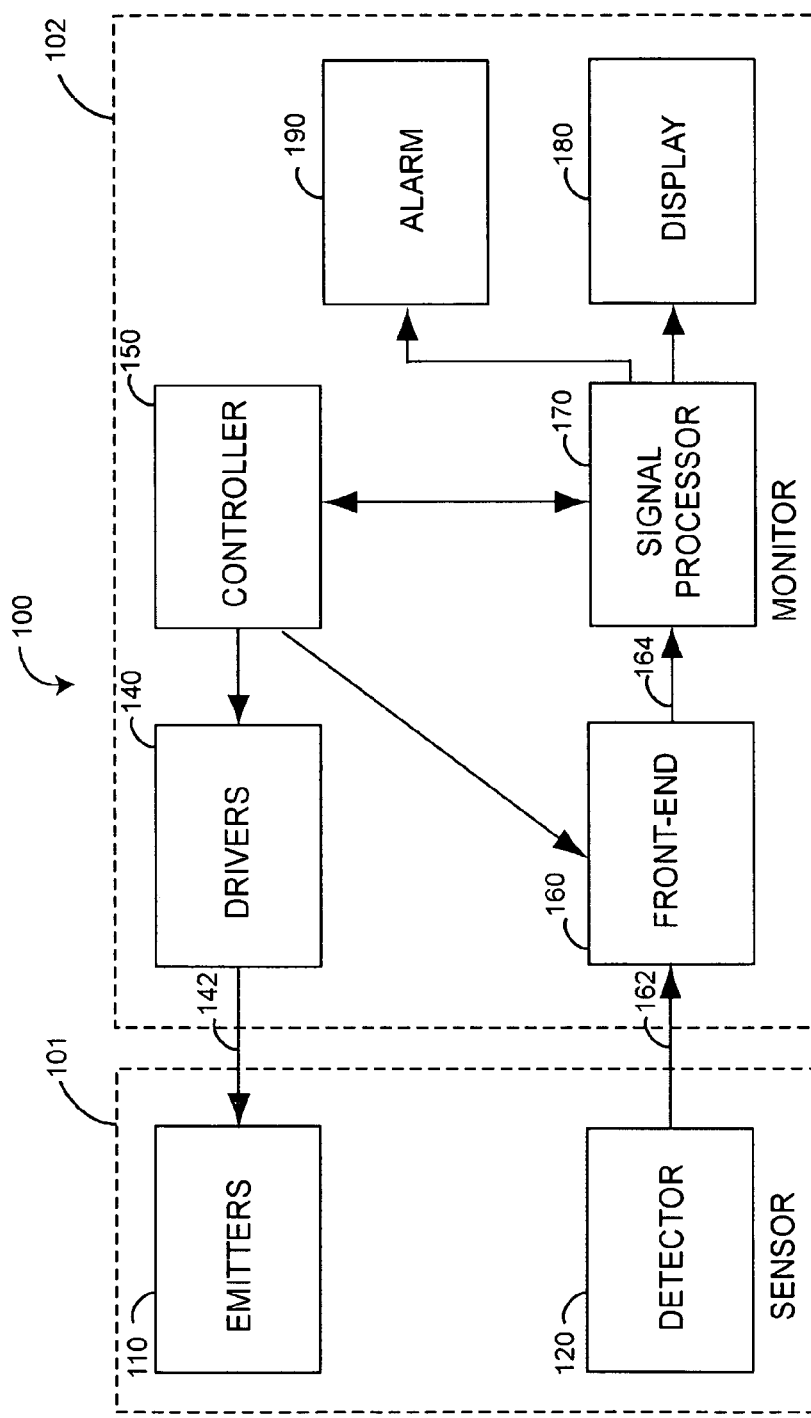
FIG. 1 is a block diagram of a conventional pulse oximeter.
Figure 2:
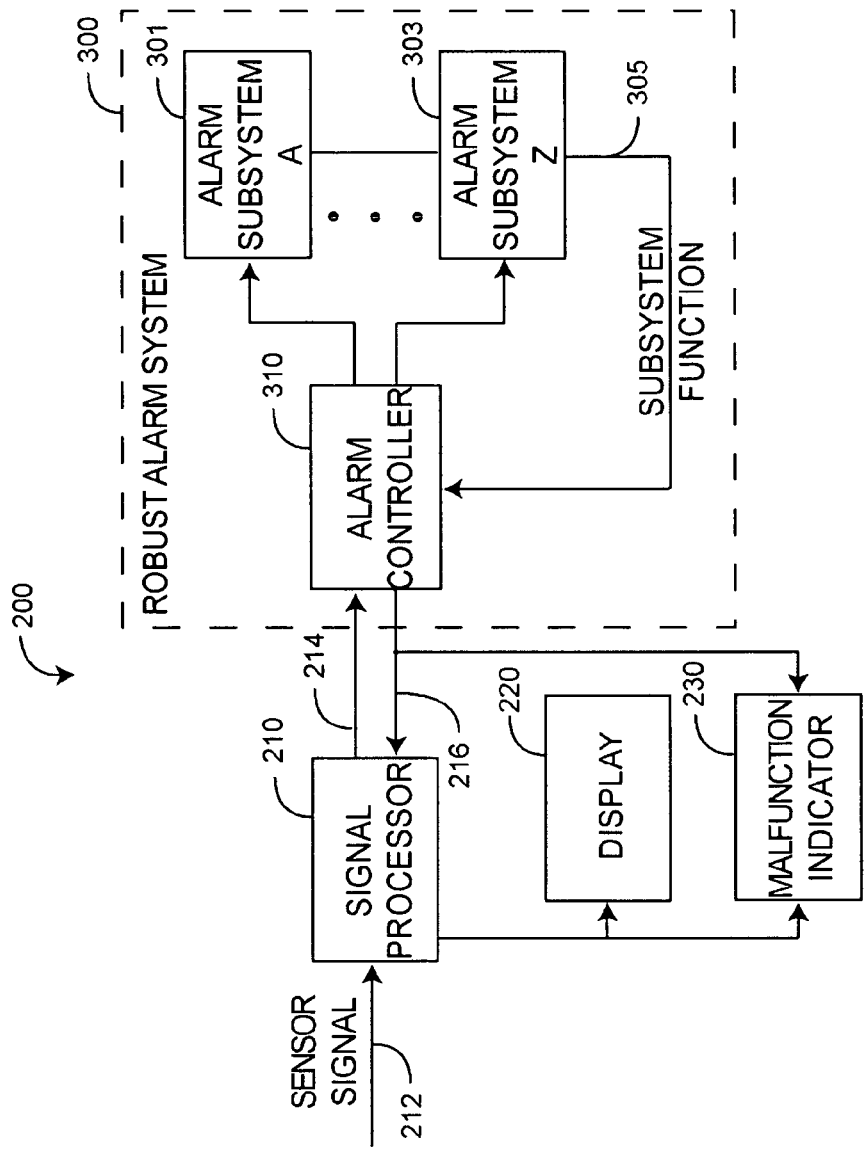
FIG. 2 is a block diagram of a physiological measurement system having a robust alarm system.

FIG. 2 illustrates a physiological measurement system 200 having a robust alarm system 300. The physiological measurement system 200 has a signal processor 210 responsive to an input sensor signal 212 and a display 220 for presenting the results. For example, the signal processor 210 may be part of a pulse oximetry monitor that is responsive to an intensity signal from an optical sensor, as described above. Likewise, the display 220 may provide a numerical indication of oxygen saturation and pulse rate calculated accordingly. Unlike a conventional alarm 190 (FIG. 1), however, the robust alarm system 300 advantageously has redundant alarms and alarm system integrity checks, as described below.

As shown in FIG. 2, the signal processor 210 inputs the sensor signal 212 and generates an alarm trigger 214 in response, such as when a parameter calculated by the signal processor is outside of predetermined limits. The alarm system 300 inputs the alarm trigger signal 214 and activates one or more alarms accordingly, as described below. In one embodiment, the alarm system 300 also outputs a malfunction signal 216, which indicates that one or more alarm subsystems 301-303 are unresponsive, i.e. are not generating an alarm in response to the alarm trigger 214. In one embodiment, the malfunction signal 216 is output to the signal processor 210, which may trigger a malfunction indication on the display 220 or trigger a separate malfunction indicator 230, or both. In another embodiment, the malfunction signal 216 is output directly to the malfunction indicator 230. The malfunction indicator 230 may be an audible alert, visual alert or alert signal. An audible alert, for example, may be an alarm, buzzer, recorded or synthesized voice to name a few. A visual alert may be a flashing light or display message, for example. An alert signal may be, for instance, an electronic signal, code or message sent to another system via wired or wireless communication channels, or local area or wide area networks, to name a few.

Also shown in FIG. 2, the robust alarm system 300 has an alarm controller 310 and one or more alarm subsystems 301-303. The alarm controller 310 inputs the alarm trigger 310 and activates an alarm subsystem 301-303 or multiple alarm subsystems concurrently. The alarm controller 310 also receives a subsystem function signal 305 that provides feedback to the alarm controller 310 as to the integrity of the alarm subsystems 301-303. In one embodiment, the subsystem function signal 305 comprises circuit function signals 332 (FIG. 3) or alarm function signals 352 (FIG. 3) or both, as described with respect to FIG. 3, below. The alarm controller 310 generates the malfunction signal 216 if alarm subsystem integrity has been compromised. In one embodiment, the malfunction signal 216 is encoded or otherwise configured so as to indicate a particular fault type or fault location or both. The fault location may be subsystem, component or subcomponent specific. In a particular embodiment, the alarm controller 310 may activate or deactivate one or more alarm subsystems 301-303 in response to the subsystem function signal 305 so as to work around one or more faulty alarm subsystems 301-303. In various embodiments, the alarm controller 310 may comprise separate hardware, software or firmware components or may be integrated with the signal processor 210. A robust alarm system 300 may be incorporated into a pulse oximeter, such as is described in detail with respect to FIG. 10, below.

Further shown in FIG. 2, the robust alarm system 300 can be configured for various self-testing, fault correction and alarm condition response. In one embodiment, two or more alarm subsystems 301-303 can be concurrently activated so that multiple alarms sound simultaneously and so that failure of any one alarm or alarm subsystem 301-303 will not result in silence during an alarm condition. These multiple alarms may each sound at different frequencies or frequency spectra so as to facilitate alarm failure recognition and troubleshooting. In another embodiment, the alarm controller 310 deactivates a failing alarm subsystem 301-303 and activates one or more redundant alarm subsystems 301-303 in response to the subsystem function signal 305. In yet another embodiment, the alarm controller 310 initiates alarm subsystem testing in the absence of an alarm condition by intermittently activating the alarm subsystems 301-303. In particular embodiments, intermittent test alarms are activated only long enough for subsystem function 305 feedback or at frequencies outside of a normal hearing range so as to be essentially unnoticeable by caregivers, patients or other personnel operating the physiological measurement system 200.

Figure 3:
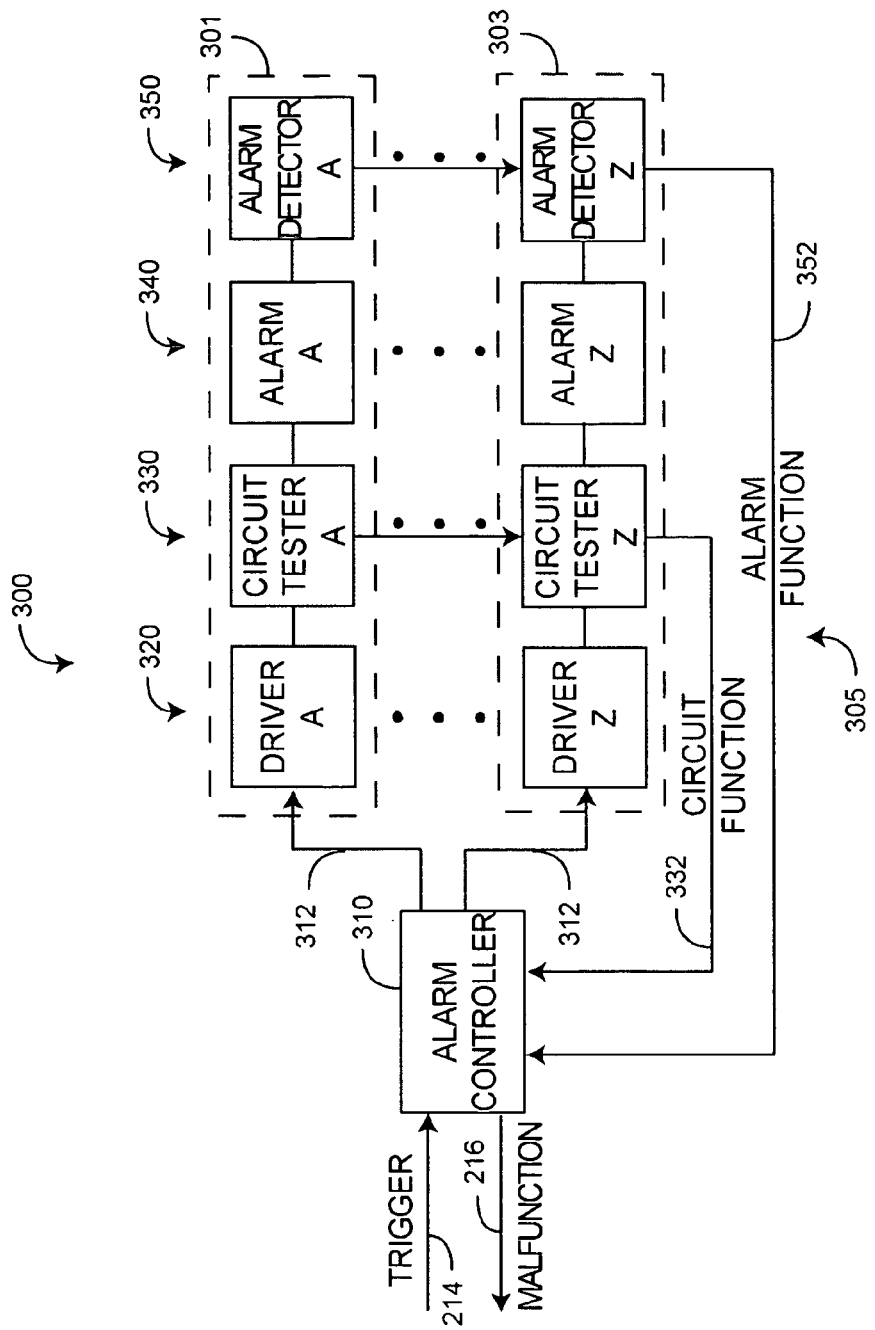
FIG. 3 is a block diagram of a robust alarm system.

FIG. 3 illustrates a robust alarm system 300 having an alarm controller 310, drivers 320, circuit testers 330, alarms 340 and detectors 350. The alarm controller 310 responds to the alarm trigger 214 by outputting drive signals 312 to one or more drivers 320 so as to activate one or more of the alarms 340. The alarms 340 may be any of various audible transducers, such as speakers, piezoelectric transducers, buzzers or bells to name a few.

As shown in FIG. 3, circuit testers 330 are in electrical communication with the drivers 320 so as to verify the integrity of the drive circuits between the drivers 320 and the alarms 340. Circuit testers 330 provide one or more circuit function signals 332 to the alarm controller 310, which the alarm controller 310 utilizes to indicate and adapt to subsystem malfunctions, as described above. A circuit tester embodiment is described with respect to FIG. 4, below.

Also shown in FIG. 3, alarm detectors 350 interface with the alarms 340 so as to verify the integrity of the alarm transducers. Alarm detectors 350 provide one or more alarm function signals 352 to the alarm controller 310, which the alarm controller 310 utilizes to indicate and adapt to subsystem malfunctions, as described above. Alarm detector embodiments are described with respect to FIGS. 5-9, below.

In one embodiment, each alarm 340 has a corresponding alarm detector 350 so that the alarm controller 310 can identify a specific malfunctioning alarm. In another embodiment, a robust alarm system 300 may have one alarm detector 350 for multiple alarms 340 that each output a unique audio frequency or frequency spectrum so as to distinguish a malfunctioning alarm. In yet another embodiment, a robust alarm system 300 may have one alarm detector 350 for all alarms 340, where each alarm is sequentially and briefly activated during a periodic or intermittent testing procedure so as to determine the existence of any malfunctioning alarms. In this manner, the detector 350 provides the alarm controller 310 with sequential alarm function signals 352. Advantageously, a combination of alarm redundancy, a drive circuit integrity check and an alarm integrity check increases overall alarm reliability.

Figure 4:
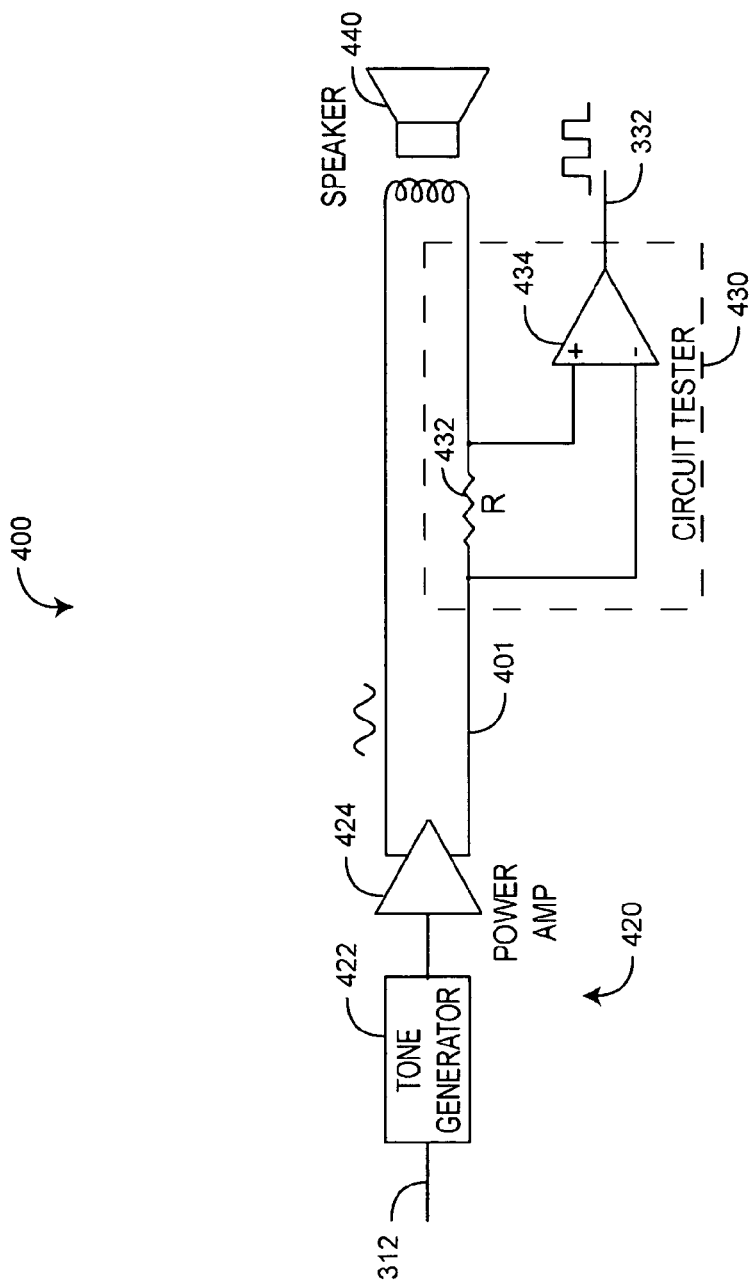
FIG. 4 is a schematic diagram of a drive circuit tester.

FIG. 4 illustrates a driver embodiment 420 and a corresponding circuit tester embodiment 430. The driver 420 comprises an oscillator 422 responsive to a drive signal 312 and a power amplifier 424 that drives a speaker 440. An alarm sounds when the alarm controller 310 (FIG. 3) activates the drive signal 312 and the speaker 440 generates a tone at the oscillator frequency. The circuit tester 430 comprises a resistor R 432 and a differential amplifier 434. The resistor 432 senses the power amplifier current flowing through the speaker coil, and the differential amplifier 434 amplifies the corresponding voltage drop across the resistor 422 providing a square wave, for example, as a circuit function signal 332 to the alarm controller 310 (FIG. 3). The alarm controller 310 (FIG. 3) verifies the integrity of the circuit between driver 420 and alarm 440 by sensing a square wave in the circuit function signal 332 when the drive signal 312 is active. Likewise, the alarm controller 310 (FIG. 3) senses a circuit malfunction if the circuit function signal 332 is a DC level or random noise when the drive signal 312 is active, such as when the tone generator or power amplifier are non-functional or when the drive circuit is open loop due to coil wire breakage. The circuit tester 430, however, cannot verify alarm integrity, i.e. that the speaker 440 is actually generating sound in response to drive current through an intact speaker coil. For example, the speaker cone may be detached from the speaker coil or otherwise damaged. Alarm detectors 350 (FIG. 3) that can verify alarm integrity are described with respect to FIGS. 5-9, below.

Figure 5:
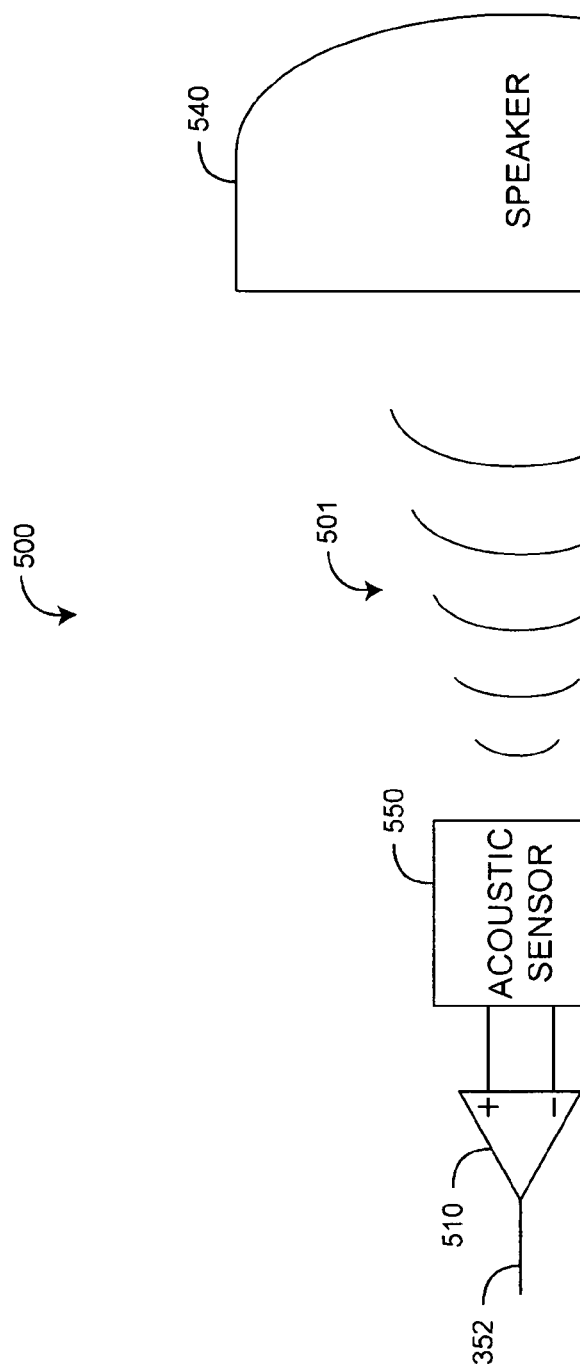
FIG. 5 is a block diagram of an acoustic sensor of alarm integrity.

FIG. 5 illustrates one embodiment of an alarm detector 350 (FIG. 3) that can verify alarm integrity. An acoustic sensor 550, such as a microphone, is configured to detect sound waves 501 generated by the alarm transducer 340 (FIG. 3), such as a speaker. An amplifier 510 generates a corresponding alarm function signal 352 to the alarm controller 310 (FIG. 3). If the alarm 540 is operative, the alarm controller 310 (FIG. 3) can detect a corresponding tone waveform in the alarm function signal 352 upon activation of the drive signal 312 (FIG. 3). Otherwise, an alarm malfunction is determined and the alarm controller 310 (FIG. 3) responds accordingly, such as generating a malfunction signal 216 (FIG. 3) or activating a redundant alarm 340 (FIG. 3) or both.

Figure 6:
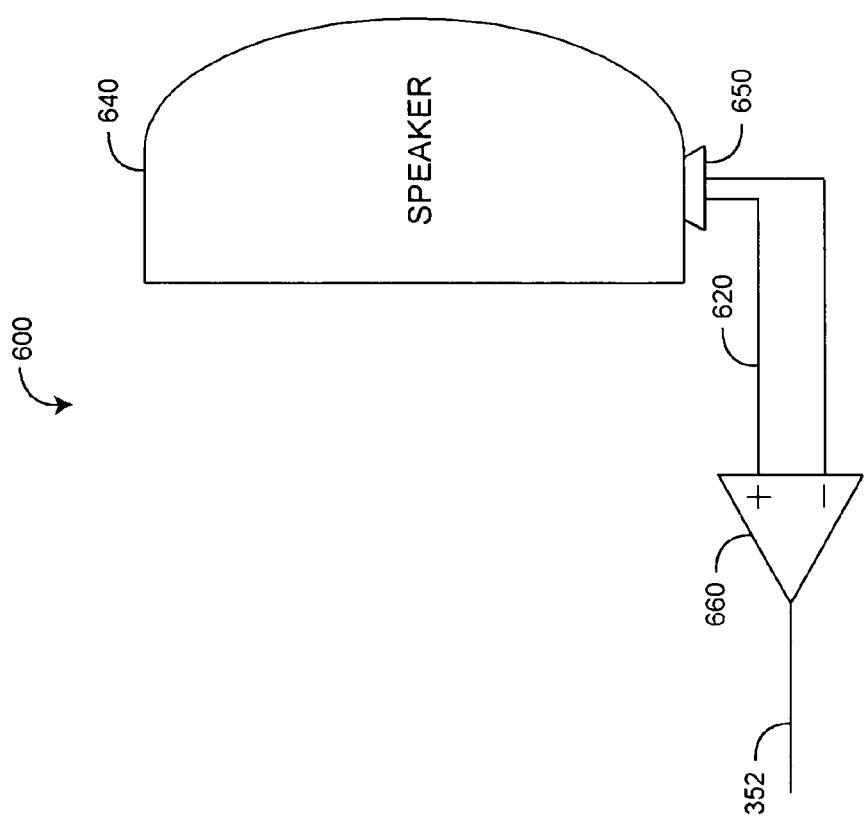
FIG. 6 is a block diagram of a piezoelectric sensor of alarm integrity.

FIG. 6 illustrates another embodiment of an alarm detector 350 (FIG. 3). A piezoelectric device 650 is configured to sense vibrations from a functioning acoustic transducer, such as a speaker 640. In particular, the piezoelectric device 650 is attached to or otherwise mechanically coupled to an acoustic transducer, such as a speaker 640. If the alarm 640 is operative, the alarm controller 310 (FIG. 3) can detect a corresponding vibration waveform in the alarm function signal 352 upon activation of the drive signal 312 (FIG. 3). Otherwise, an alarm malfunction is determined and the alarm controller 310 (FIG. 3) responds accordingly.

Figure 7:
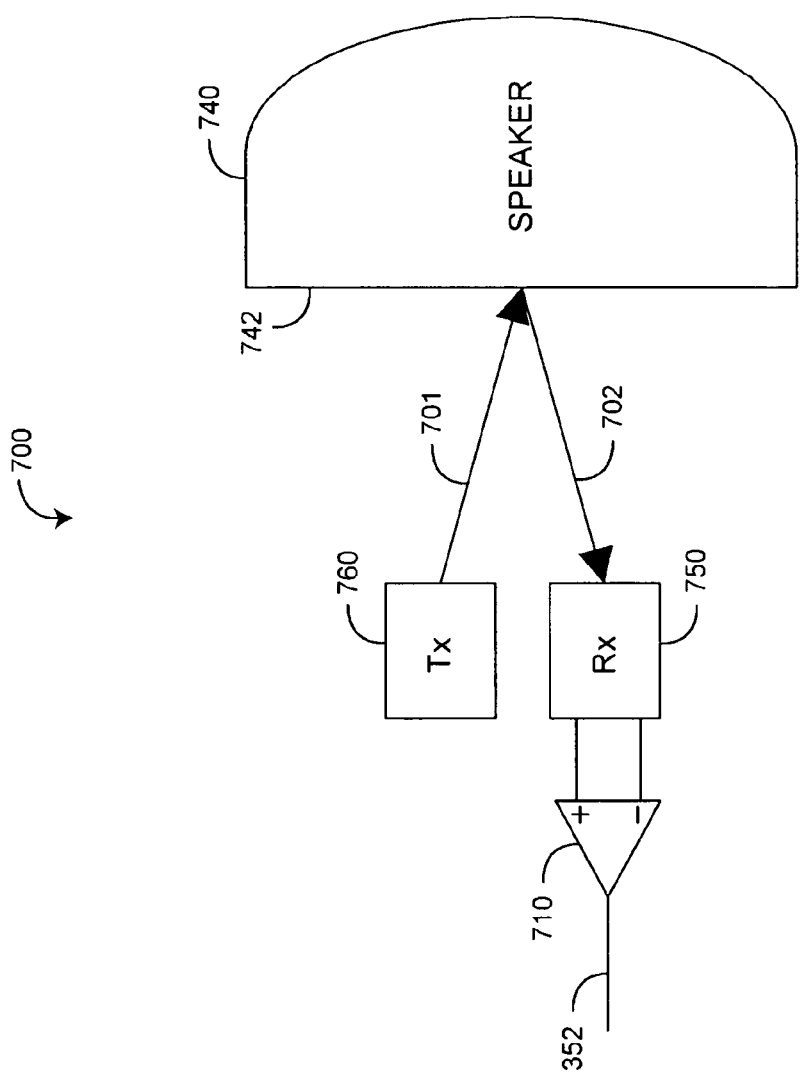
FIG. 7 is a block diagram of a ultrasound sensor of alarm integrity.

FIG. 7 illustrates a further embodiment of an alarm detector 350 (FIG. 3). An ultrasound transmitter 760 and corresponding ultrasound receiver 750 are configured to sense movement from a functioning acoustic transducer, such a speaker 740. In particular, the transmitter 760 is adapted to transmit an ultrasound wave 701 to the speaker cone 742. The receiver 750 is adapted to measure a return ultrasound wave 702 reflected off of the cone 742. If the speaker cone 742 is in motion, the return ultrasound wave 702 is phase shifted from the transmitted ultrasound wave 701 due to changes in the ultrasound wave path length and frequency shifted due to the Doppler effect. If the speaker cone 742 is motionless, the return ultrasound wave 702 is a steady sinusoidal with the same frequency as the transmitted ultrasound wave 701. Thus, if the alarm 740 is operative, the alarm controller 310 (FIG. 3) can detect these phase and frequency shifts as reflected in the alarm function signal 352 upon activation of the drive signal 312 (FIG. 3). Otherwise, an alarm malfunction is determined and the alarm controller 310 (FIG. 3) responds accordingly.

Figure 8:
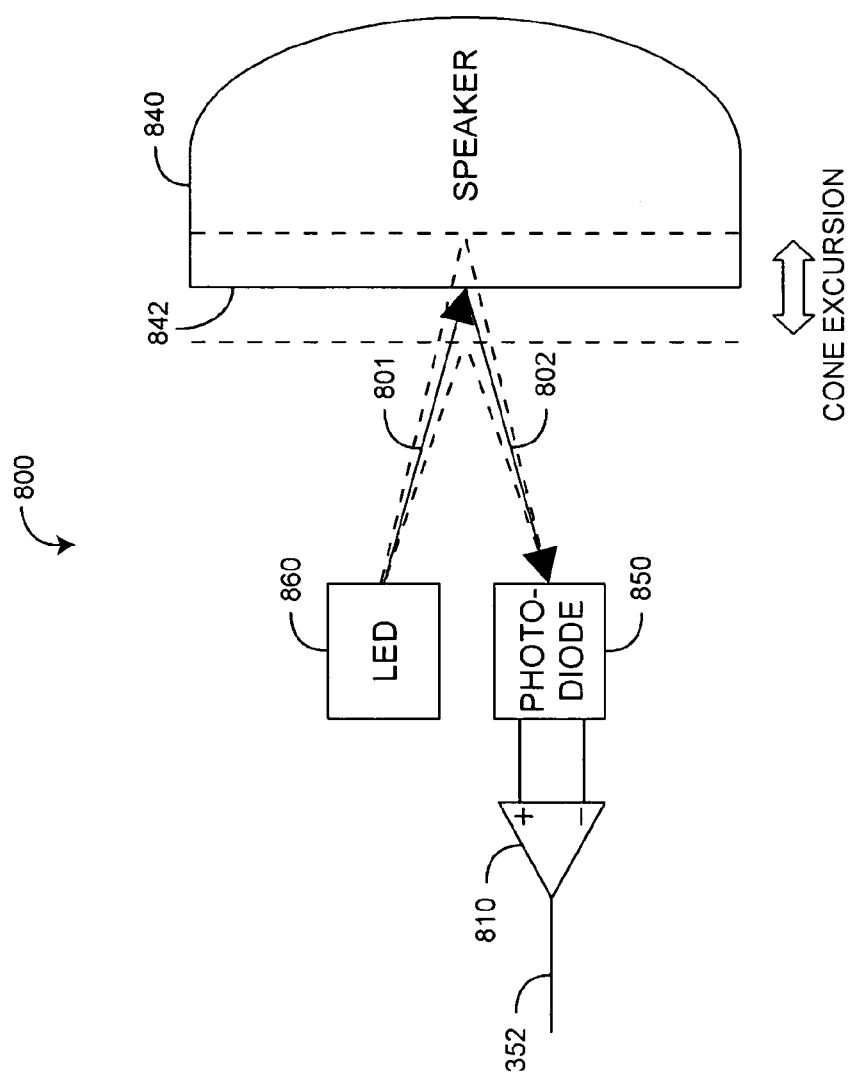
FIG. 8 is a block diagram of an optical sensor of alarm integrity.

FIG. 8 illustrates yet another embodiment of an alarm detector 350 (FIG. 3). An LED emitter 860 and a photodiode sensor 850 are configured to sense movement from a functioning acoustic transducer, such a speaker 840. In particular, a DC signal is applied to the LED 840, which is adapted to emit light 801 so as to illuminate a portion of the speaker cone 842. The photodiode 850 is adapted to detect the intensity of light reflected 802 off of the speaker cone 842. If the speaker cone 842 is in motion, the light intensity at the photodiode 850 will have an AC component because of changes that occur in the LED-photodiode focal point and optical path. Further, if the speaker cone 842 has small excursions, the AC component of the light intensity at photodiode will have a frequency spectra corresponding to that of the speaker 840, which allows the sound frequency spectra generated by the speaker 840 to be verified. If the speaker cone 842 is motionless, the light intensity at the photodiode will be a DC value. Thus, if the alarm 840 is operative, the alarm controller 310 (FIG. 3) can detect these phase and frequency shifts as reflected in the alarm function signal 352 upon activation of the drive signal 312 (FIG. 3). Otherwise, an alarm malfunction is determined and the alarm controller 310 (FIG. 3) responds accordingly. In an alternative embodiment, a modulated signal is applied to the LED 860 and a corresponding demodulation is applied to the photodiode 850 so as to detect the AC component due to speaker cone motion.

Figure 9:
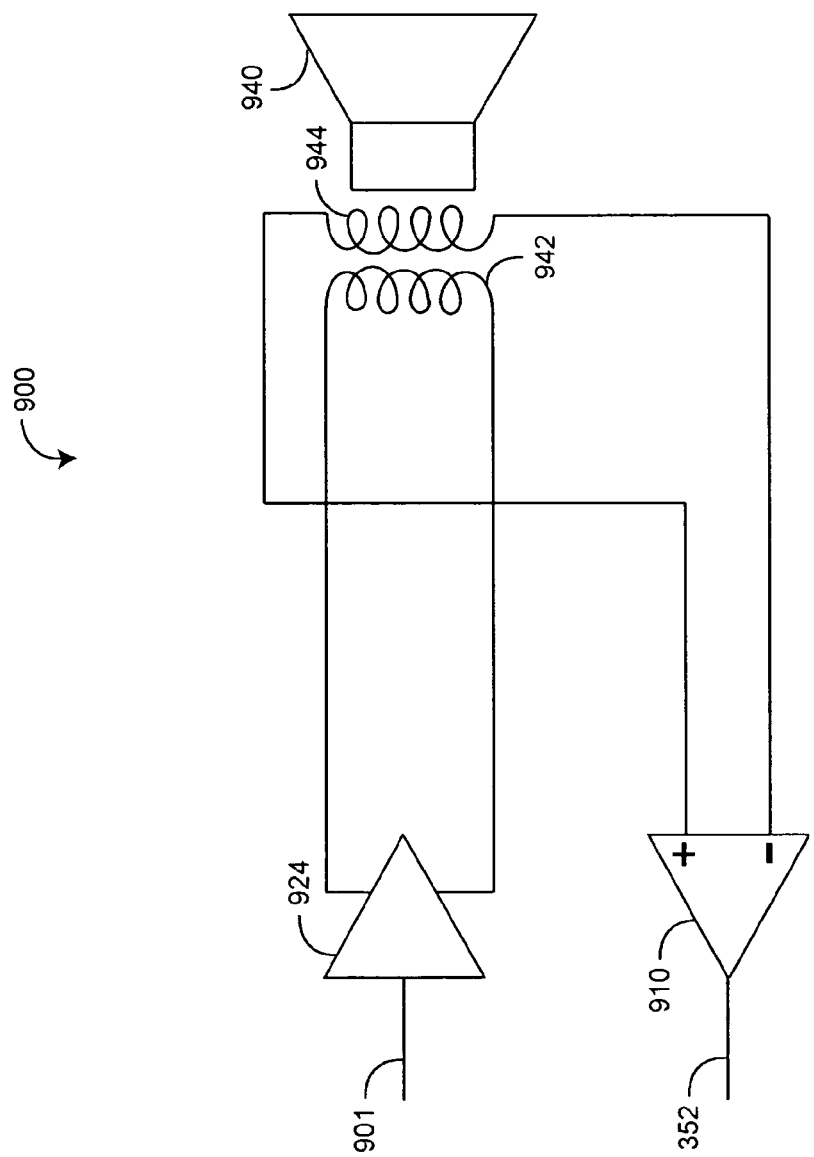
FIG. 9 is a block diagram of an tandem speaker coil sensor of alarm integrity.

FIG. 9 illustrates an additional embodiment of an alarm detector 350 (FIG. 3). A sensing coil 944 is configured to sense movement in a functioning acoustic transducer, such a speaker 940. In particular, the sensing coil 944 is placed in tandem with the speaker coil 942 so that movement of the speaker cone resulting from drive current in the speaker coil 942 induces current in the sensing coil 944. That is, movement of the sensing coil 944 through the field of the speaker magnet results in a corresponding current in the sensing coil 944. Thus, if the speaker 940 is operative, the alarm controller 310 (FIG. 3) can detect the sensing coil 944 current in the alarm function signal 352 upon activation of the drive signal 312 (FIG. 3) and a corresponding tone generator input 901 to the speaker amplifier 924. Otherwise, an alarm malfunction is determined and the alarm controller 310 (FIG. 3) responds accordingly.

Figure 10:
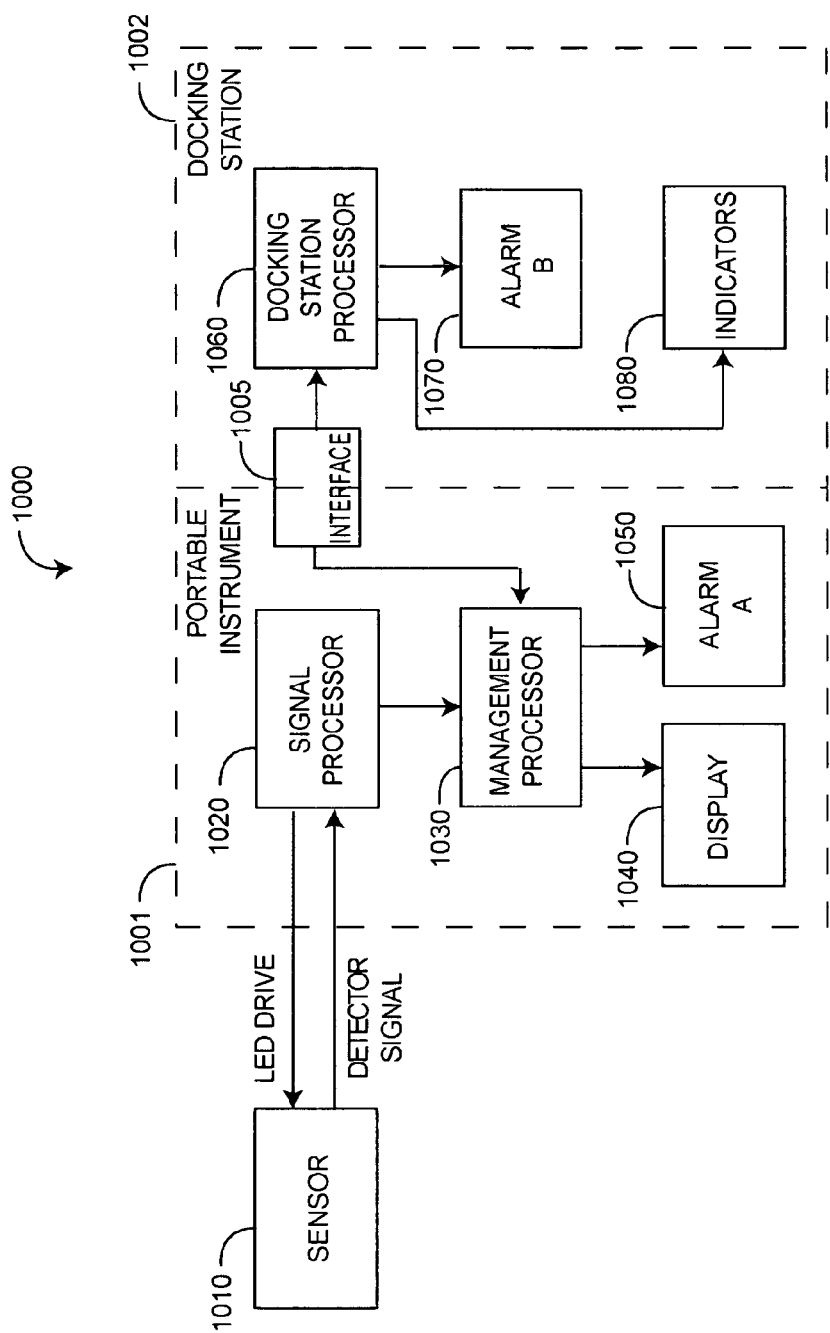
FIG. 10 is a block diagram of a pulse oximeter comprising a portable instrument, and corresponding docking station incorporating a robust alarm system.

FIG. 10 illustrates a pulse oximeter 1000 comprising a portable instrument 1001 and a corresponding docking station 1002. Advantageously, when the portable instrument 1001 is docked, the pulse oximeter 1000 has redundant alarms 1050, 1070 that are activated concurrently so as to provide a robust alarm system. In particular, failure of one alarm does not silence an audible indication of a measured parameter outside of preset limits, such as during a desaturation event. Further, concurrent activation of the alarms 1050, 1070 provides a stereo-like directional resolution that allows a caregiver in a large ward to more readily locate the pulse oximeter and the patient corresponding to the alarm.

As shown in FIG. 10, the portable instrument 1001 has a signal processor 1020 in communications with a sensor 1010, a management processor 1030, a display 1040 and an alarm A 1050. The signal processor 1020 functions in conjunction with the sensor 1010 to determine oxygen saturation, pulse rate and related parameters, as described above. These results are communicated to the display 1040 and alarm A 1050 via the management processor 1030. The docking station 1002 has a processor 1060, an alarm B 1070 and various visual status indicators 1080. The portable instrument 1001 and docking station 1002 communicate across a mechanical and electrical interface 1005 via their respective processors 1030, 1060. In particular, an alarm condition determined by the portable's management processor 1030 is communicated to the docking station processor 1060 for concurrent activation of alarms A and B 1050, 1070. A pulse oximetry comprising a portable instrument and a docking station are described in U.S. Pat. No. 6,584,336 entitled Universal/Upgrading Pulse Oximeter, which is assigned to Masimo Corporation, Irvine, Calif. and incorporated by reference herein.

A pulse oximeter having a robust alarm system is described above as a combination portable instrument and docking station having multiple, concurrently activated alarms. In other embodiments, a pulse oximeter having multiple, concurrently activated alarms may be a single standalone instrument, handheld or plug-in module, as further examples. A robust alarm system is also described above as having audible alarm transducers and corresponding alarm detectors. In other embodiments, the alarms may be audible or visual or a combination of both and the alarm detectors may be any of various optical devices for verifying operation of visual indictors or displays.

A robust alarm system has been disclosed in detail in connection with various embodiments. These embodiments are disclosed by way of examples only and are not to limit the scope of the claims that follow. One of ordinary skill in art will appreciate many variations and modifications.

What is claimed is:

1. A method of providing audio or visual alarms for a patient monitor, said method executed on one or more processors of said patient monitor to provide patient monitoring functionality including determining measurements for one or more physiological parameters of a patient and when desired, alerting one or more caregivers that said measurements meet one or more predetermined conditions, said method comprising:

outputting a drive signal configured to cause a light source of a noninvasive sensor to emit optical radiation having at least two wavelengths into a tissue site of said patient;

receiving a sensor signal from said sensor, said sensor signal responsive to attenuation of said optical radiation by said tissue site;

electronically determining a physiological parameter measurement responsive to said sensor signal;

generating an alarm trigger responsive to said physiological parameter measurement being beyond a preset limit of said physiological parameter;

determining an availability of a first alarm, said determining comprising monitoring an alarm drive circuit associated with said first alarm to verify said circuit's integrity; and activating a second alarm in response to said trigger and a determination that said first alarm is unavailable.

2. The method according to claim 1 wherein said determining comprises monitoring an alarm transducer associated with said first alarm to verify said transducer's integrity.

3. A method of providing audio or visual alarms for a patient monitor, said method executed on one or more processors of said patient monitor to provide patient monitoring functionality including determining measurements for one or more physiological parameters of a patient and when desired, alerting one or more caregivers that said measurements meet one or more predetermined conditions, said comprising:

outputting a drive signal configured to cause a light source of a noninvasive sensor to emit optical radiation having at least two wavelengths into a tissue site of said patient;

receiving a sensor signal from said sensor, said sensor signal responsive to attenuation of said optical radiation by said tissue site;

electronically determining a physiological parameter measurement responsive to said sensor signal;

generating an alarm trigger responsive to said physiological parameter measurement being beyond a preset limit of said physiological parameter;

determining an availability of a first alarm;

activating a second alarm in response to said trigger and a determination that said first alarm is unavailable;

distributing at least said a first alarms to a portable instrument; and distributing at least said second alarms to a docking station adapted to mechanically and electrically interface with said portable instrument.

4. A patient monitor configured to monitor one or more physiological parameters of a patient to alert one or more caregivers when said monitored parameters meet predetermined conditions and configured to include a portable housing dockable with a docking station, comprising:

a portable housing including a sensor output configured to carry a drive signal capable of causing a light source of a physiological sensor to emit optical radiation having at least two wavelengths into tissue of said patient;

said portable housing including an input configured to receive a sensor signal from said sensor, said sensor signal responsive to attenuation of said optical radiation by said tissue;

said portable housing including one or more signal processors configured to determine measurements of said parameters responsive to said sensor signal, and generate an alarm trigger responsive to said measurements;

said portable housing including a first alarm mechanism; and a docking station configured to mechanically and electrically mate with said portable housing, said docking station including a second alarm mechanism responsive to said trigger and activated based on a determination that said first alarm mechanism is unavailable.

5. The patient monitor according to claim 4, comprising alarm integrity circuits, each configured to determine an availability of one of said alarm mechanisms.

6. The patient monitor according to claim 5 wherein each of said alarm integrity circuits comprises an acoustic sensor.

7. The patient monitor according to claim 5 wherein each of said alarm integrity circuits comprises a piezoelectric sensor.

8. The patient monitor according to claim 7 wherein each piezoelectric sensor is mechanically coupled to a corresponding alarm mechanism to detect vibrations therefrom.

9. The patient monitor according to claim 5 wherein each of said alarm integrity circuits comprises an ultrasound sensor.

10. A patient monitor configured to monitor one or more physiological parameters of a patient to alert one or more caregivers when said monitored parameters meet predetermined conditions, comprising:

a sensor output configured to carry a drive signal capable of causing a light source of a physiological sensor to emit optical radiation having at least two wavelengths into tissue of said patient;

an input configured to receive a sensor signal from said sensor, said sensor signal responsive to attenuation of said optical radiation by said tissue;

one or more signal processors configured to determine measurements of said parameters responsive to said sensor signal, and generate an alarm trigger responsive to said measurements when said measurements are in an alarm condition;

a first alarm mechanism comprising a driving circuit, an audiovisual device driven by said driving circuit when said alarm trigger is generated during said alarm condition, a drive integrity circuit configured to determine whether said driving circuit is operational, and a device integrity circuit configured to determine whether said audiovisual device is operational; and a second alarm mechanism responsive to said alarm trigger and activated based on a determination by one or more of said drive integrity circuit or said device integrity circuit that said first alarm mechanism is unavailable.

11. The patient monitor of claim 10, wherein said first alarm mechanism is incorporated into a portable device and said second alarm mechanism is incorporated into a charging station for said portable device.

* * * * *

UNITED STATES PATENT AND TRADEMARK OFFICE
CERTIFICATE OF CORRECTION

Page 1 of 2

PATENT NO. : 7,962,188 B2
APPLICATION NO. : 11/546927
DATED : June 14, 2011
INVENTOR(S) : Massi Joseph E. Kiani et al.

It is certified that error appears in the above-identified patent and that said Letters Patent is hereby corrected as shown below:

At the list of references on Page 2, column 2, line 22, please delete "Al-All" and insert therefore, --Al-Ali--.

At Figure 1, after "FIG. 1" please add --(Prior Art)--.

The sheet of drawing consisting of figure 1 should be deleted and substituted for the drawing shown below:

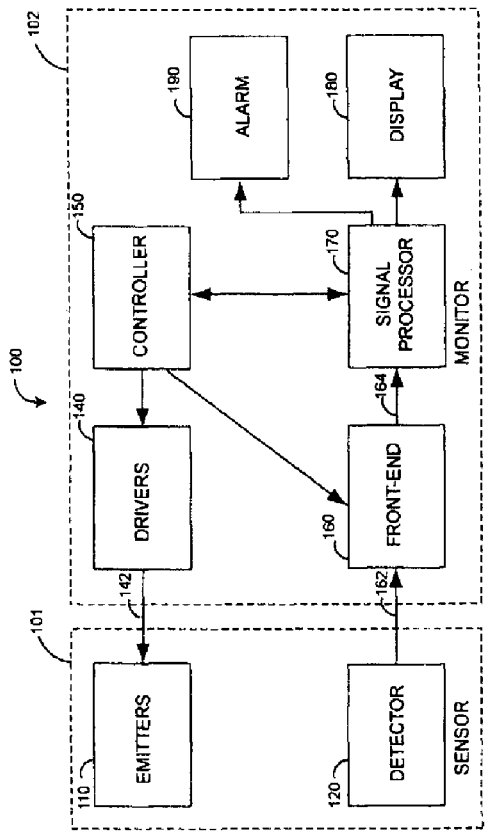

Signed and Sealed this
Third Day of July, 2012

David J. Kappos
*Director of the United States Patent and Trademark Office*

CERTIFICATE OF CORRECTION (continued)
U.S. Pat. No. 7,962,188 B2

At Claim 3, column 7, line 32, please delete "said" and insert therefore, --said method--.

At Claim 3, column 7, line 46, please delete "a first alarms" and insert therefore, --first alarm--.

At Claim 3, column 7, line 48, please delete "alarms" and insert therefore, --alarm--.

US007962188C1

(12) EX PARTE REEXAMINATION CERTIFICATE (9720th)
United States Patent
Kiani et al.

(10) Number: US 7,962,188 C1
(45) Certificate Issued: Jun. 26, 2013

(54) ROBUST ALARM SYSTEM

(75) Inventors: Massi Joseph E. Kiani, Laguna Niguel, CA (US); Mohamed Kheir Diab, Mission Viejo, CA (US); Marcelo M. Lamego, Irvine, CA (US)

(73) Assignee: Masimo Corporation, Irvine, CA (US)

Reexamination Request:
No. 90/012,534, Sep. 13, 2012

Reexamination Certificate for:
Patent No.: 7,962,188
Issued: Jun. 14, 2011
Appl. No.: 11/546,927
Filed: Oct. 12, 2006

Certificate of Correction issued Jul. 3, 2012

Related U.S. Application Data

(60) Provisional application No. 60/726,638, filed on Oct. 14, 2005.

(51) Int. Cl.
*A61B 5/00* (2006.01)

(52) U.S. Cl.
USPC ............ 600/309; 600/322; 600/323; 600/324

(58) Field of Classification Search
None
See application file for complete search history.

(56) References Cited

To view the complete listing of prior art documents cited during the proceeding for Reexamination Control Number 90/012,534, please refer to the USPTO's public Patent Application Information Retrieval (PAIR) system under the Display References tab.

*Primary Examiner* — Robert Nasser

(57) ABSTRACT

A robust alarm system has an alarm controller adapted to input an alarm trigger and to generate at least one alarm drive signal in response. Alarm subsystems input the alarm drive signal and activate one or more of multiple alarms accordingly. A subsystem function signal provides feedback to the alarm controller as to alarm subsystem integrity. A malfunction indicator is output from the alarm controller in response to a failure within the alarm subsystems.

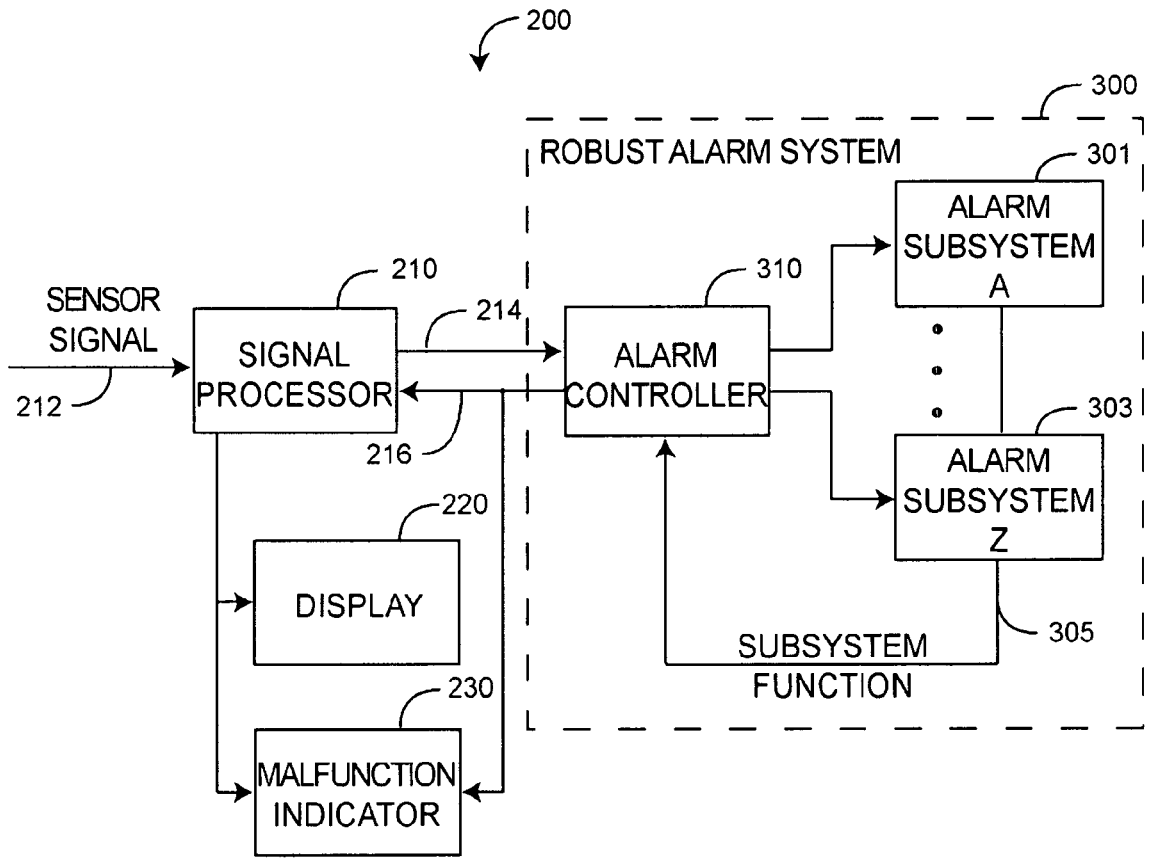

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 9-11 are cancelled.

Claims 3, 4 and 8 are determined to be patentable as amended.

Claims 5-7, dependent on an amended claim, are determined to be patentable.

3. A method of providing audio or visual alarms for a patient monitor, said method executed on one or more processors of said patient monitor to provide patient monitoring functionality including determining measurements for one or more physiological parameters of a patient and when desired, alerting one or more caregivers that said measurements meet one or more predetermined conditions, said *method* comprising:

outputting a drive signal configured to cause a light source of a noninvasive sensor to emit optical radiation having at least two wavelengths into a tissue site of said patient;

receiving a sensor signal from said sensor, said sensor signal responsive to attenuation of said optical radiation by said tissue site;

electronically determining a physiological parameter measurement responsive to said sensor signal;

generating an alarm trigger responsive to said physiological parameter measurement being beyond a preset limit of said physiological parameter;

determining an availability of a first alarm *configured to provide an audible alert at said patient monitor*;

activating a second alarm *configured to provide an audible alert at said patient monitor*, in response to said trigger and a determination that said first alarm is unavailable;

distributing at least said first alarm to a portable instrument; and distributing at least said second alarm to a docking station adapted to mechanically and electrically interface with said portable instrument.

4. A patient monitor configured to monitor one or more physiological parameters of a patient to alert one or more caregivers when said monitored parameters meet predetermined conditions and configured to include a portable housing dockable with a docking station, comprising:

a portable housing including a sensor output configured to carry a drive signal capable of causing a light source of a physiological sensor to emit optical radiation having at least two wavelengths into tissue of said patient;

said portable housing including an input configured to receive a sensor signal from said sensor, said sensor signal responsive to attenuation of said optical radiation by said tissue;

said portable housing including one or more signal processors configured to determine measurements of said parameters responsive to said sensor signal, and generate an alarm trigger responsive to said measurements;

said portable housing including a first alarm mechanism *configured to provide an audible alert at said patient monitor*; and a docking station configured to mechanically and electrically mate with said portable housing, said docking station including a second alarm mechanism *configured to provide an audible alert at said patient monitor and* responsive to said trigger and activated based on a determination that said first alarm mechanism is unavailable.

8. [The patient monitor according to claim 7] *A patient monitor configured to monitor one or more physiological parameters of a patient to alert one or more caregivers when said monitored parameters meet predetermined conditions and configured to include a portable housing dockable with a docking station, comprising:*

*a portable housing including a sensor output configured to carry a drive signal capable of causing a light source of a physiological sensor to emit optical radiation having at least two wavelengths into tissue of said patient;*

*said portable housing including an input configured to receive a sensor signal from said sensor, said sensor signal responsive to attenuation of said optical radiation by said tissue;*

*said portable housing including one or more signal processors configured to determine measurements of said parameters responsive to said sensor signal, and* generate an alarm trigger responsive to said measurements;

*said portable housing including a first alarm mechanism;*

*a docking station configured to mechanically and electrically mate with said portable housing, said docking station including a second alarm mechanism responsive to said trigger and activated based on a determination that said first alarm mechanism is unavailable; and*

*alarm integrity circuits, each configured to determine an availability of one of said alarm mechanisms, wherein each of said alarm integrity circuits comprises a piezoelectric sensor, wherein each piezoelectric sensor is mechanically coupled to a corresponding alarm mechanism to detect vibrations therefrom.*

\* \* \* \* \*